United States Patent [19]
Willingham

[11] Patent Number: 5,094,957
[45] Date of Patent: Mar. 10, 1992

[54] QUANTITATIVE METHOD FOR DETERMINING CONCENTRATION OF 3-ISOTHIAZOLONE

[75] Inventor: Gary L. Willingham, Glenside, Pa.

[73] Assignee: Rohm and Haas Company, Philadelphia, Pa.

[21] Appl. No.: 625,274

[22] Filed: Dec. 10, 1990

[51] Int. Cl.$^5$ .............................................. G01N 21/78
[52] U.S. Cl. ...................................... 436/92; 436/164
[58] Field of Search .................................. 436/92, 164

[56] References Cited

U.S. PATENT DOCUMENTS 3,975,155  8/1976  Geyer .
4,110,378  8/1978  Geyer .
4,652,530  3/1987  Rothman et al. .

Primary Examiner—Robert J. Hill, Jr.
Attorney, Agent, or Firm—Michael B. Fein

[57] ABSTRACT

A method for determining the concentration of isothiazolones in an aqueous system comprising:
(a) mixing a known volume of solution to be analyzed with a volume containing a known quantity of aromatic thiol salts which form colored solutions for a specified period of time;
(b) determining color of the resultant solution; and
(c) comparing the color to a standard of known concentration.

This invention is especially applicable to cooling towers and in the metal working industry and for fuel.

8 Claims, No Drawings

QUANTITATIVE METHOD FOR DETERMINING CONCENTRATION OF 3-ISOTHIAZOLONE

BACKGROUND OF THE INVENTION

This invention relates to a quantitative, colorimetric method for determining the concentration of isothiazolones in aqueous systems, and more particularly to a highly sensitive monitoring method for determining low concentrations of isothiazolones in aqueous systems, such as cooling tower and metal working fluids, containing other biocides, additives and contaminants.

FIELD OF THE INVENTION

Isothiazolones, as defined herein, refer to substituted and unsubstituted 3-isothiazolones and mixtures having the structural formula:

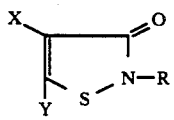

where
R is hydrogen, an unsubstituted or substituted alkyl group of 1 to 10 carbon atoms, an unsubstituted or substituted cycloalkyl group of 3 to 8 carbon atoms, an unsubstituted or substituted aralkyl group of up to 10 carbon atoms, or an unsubstituted or substituted aryl group of up to 10 carbon atoms;
X and Y are independently a hydrogen atom, a halogen atom or a $(C_1-C_4)$ alkyl group or when taken together form a substituted or unsubstituted benzene ring to give a compound of the formula:

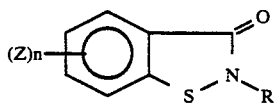

where
Z is a $(C_1-C_4)$ alkyl group, a $(C_1-C_4)$ alkoxyl group, a cyano group, a nitrogen group, or a halogen group; and
n is a integer of from zero to two.

Some of the isothiazolones present in aqueous systems may be in the form of complexed divalent salts such as magnesium or calcium.

Isothiazolones, marketed by Rohm and Haas Company and ICI under the trademarks Kathon ® and Proxel ®, respectively, are antibacterial agents or biocides which are widely used in a variety of aqueous and non-aqueous systems. For example, isothiazolones are useful as microbicides in metal working fluids and as slimicides in cooling tower water.

Attempts have been made to develop a rapid, reliable and sensitive method for determining the concentration of isothiazolones in aqueous systems for use in field applications without the need to employ sophisticated and expensive gas chromatographic, liquid chromatographic (HPLC) or ultraviolet spectrophotometric techniques. These prior field monitoring techniques have been found to be less than satisfactory because of the susceptibility of the techniques to positive and negative interferences caused by additives and ionic impurities commonly found in aqueous systems, such as cooling tower water and metal working fluids; and because of the difficulty in obtaining a high degree of sensitivity for measuring low concentrations of isothiazolones. Various additives are typically added to recirculating cooling tower water to prevent or inhibit the precipitation of hardness ions, to disperse scale, and to combat corrosion. For example, polyacrylates, phosphates, phosphonates, iron, zinc, tin and other metals are commonly found in cooling tower water as well as suspended particulate materials such as clay and silt.

U.S. Pat. Nos. 3,975,155, 4,110,378 and 4,652,530 are directed to prior colorimetric determination methods for isothiazolones in aqueous and non-aqueous systems. Both of these methods require purification of the isothiazolones to remove materials causing interference to the method.

A simple, fast and sensitive method is, therefore, desired by operators of cooling towers, metal working fluids and other aqueous systems to enable them to make economical decisions in the field concerning the timing and need for the addition of isothiazolones to their system.

It is, therefore, an object of the present invention to provide a fast, reproducible, simple and sensitive method for monitoring low concentrations of isothiazolones in aqueous systems, without the use of sophisticated and expensive instruments, so that the concentration of isothiazolones can be monitored in the field.

It is an object of the present invention to provide such a method that is specifically adapted for use with metal working fluids and cooling waters containing ionic impurities, surfactants, amines, corrosion inhibitors, and the like.

SUMMARY OF THE INVENTION

We have found that the above objectives can be realized by a novel colorimetric monitoring method comprising a method for determining the concentration of isothiazolones in an aqueous system comprising:
(a) mixing a known volume of solution to be analyzed with a volume containing a known quantity of aromatic thiol salts which form colored solutions for a specified period of time;
(b) determining color of the resultant solution; and
(c) comparing the color to a standard of known concentration.

This method is fast, simple, reproducible, and senstive to the presence of isothiazolones in aqueous systems at concentrations of about one part per million and lower. The method is particularly useful for monitoring the concentration of isothiazolones in cooling tower waters, metal working fluids, and fuels.

DETAILED DESCRIPTION OF THE INVENTION

The method of this invention is directed to the quantitative determination of low levels of isothiazolones in aqueous systems, and particularly for monitoring isothiazolones in cooling tower waters at concentrations of from about 0.1 to about 500 parts per million.

The method of the invention involves a method for determining the concentration of isothiazolones in an aqueous system comprising
(a) mixing a known volume of solution to be analyzed with a volume containing a known quantity of aromatic thiol salts which form colored solutions for a specified period of time;
(b) determining color of the resultant solution; and (c) comparing the color to a standard of known concentration.

A preferred group of aromatic thiol salts are thionitrobenzoates, thiopyridine salts, and thionicotinic salts. Specifically, 5-thio-2-nitrobenzoate, 2-thiopyridine salt, 4-thiopyridine salt, and 6-thionicotinoate are preferred salts.

A preferred method of comparing the color to a standard is by visual inspection because a spectrophotometer may be inconvenient to use at certain locations such as cooling towers or where metal working fluids are used.

The following examples are presented to illustrate a few embodiments of the invention. All parts and percentages are by weight unless otherwise indicated.

EXAMPLE 1

Example 1 demonstrates the use of the thionitrobenzoate assay (TNB assay) to measure concentrations of a 3/1 mixture of 5-chloro-2-methyl-3-isothiazolone/2-methyl-3-isothiazolone in deionized water. The isothiazolone mixture (Kathon® MW) also contained magnesium nitrate and magnesium chloride. Similar results were obtained in the absence of magnesium salts using only a pure isothiazolone mixture.

The colorimetric assay was run as follows. A 500 ppm solution of 5,5'-dithiobis(2-nitrobenzoic acid) (DTNB) was prepared in a 1/1 solution of methanol/aqueous sodium phosphate (0.01M) pH 8.0 buffer. A drop of 50% NaOH was added to convert DTNB to 5-thio-2-nitrobenzoate (TNB) anion. This solution is bright yellow. The solution was mixed with analyte solutions to yield a final TNB concentration of approximately 30 ppm.

Absorbance readings were taken at 400 ppm after 2 hr on several concentrations of isothiazolone (ITA). Results are given in Table 1. Samples could be visually differentiated.

TABLE 1

| TNB Assay ITA Concentration Curve | |
|---|---|
| ITA Concentration (ppm) | Absorbance at 400 mm |
| 0 | 1.40 |
| 5 | 1.26 |
| 10 | 1.12 |
| 15 | 0.98 |
| 20 | 0.88 |
| 25 | 0.78 |

EXAMPLE 2

Example 2 demonstrates the colorimetric response of the assay as a function of time. ITA (10 ppm ai) in buffer was mixed with a TNB solution and absorbance at 400 nm was read at various times. Results are shown in Table 2. The results show that absorbance drops rapidly over the first two hours and gradually decreases, reaching a minimum value at about 12 hours.

TABLE 2

| Absorbance at 400 nm as a function of time in the TNB assay solution containing 10 ppm ITA. | |
|---|---|
| Time (hr) | Absorbance at 400 nm |
| 0 | 1.36 |
| 0.16 | 1.14 |
| 0.32 | 1.02 |
| 2.5 | 0.98 |
| 3.5 | 0.76 |
| 4.5 | 0.64 |
| 5.5 | 0.54 |

TABLE 2-continued

| Absorbance at 400 nm as a function of time in the TNB assay solution containing 10 ppm ITA. | |
|---|---|
| Time (hr) | Absorbance at 400 nm |
| 6.5 | 0.46 |
| 7.5 | 0.40 |
| 8.5 | 0.36 |
| 9.5 | 0.32 |
| 10.5 | 0.28 |
| 11.5 | 0.26 |
| 12.5 | 0.24 |
| 13.5 | 0.20 |
| 14.5 | 0.18 |
| 15.5 | 0.18 |
| 16.5 | 0.16 |
| 17.5 | 0.16 |
| 18.5 | 0.14 |
| 19.5 | 0.12 |
| 20.5 | 0.10 |
| 21.5 | 0.10 |

EXAMPLES 3-4

Examples 3-4 demonstrates the use of the assay in metal working fluids. Samples were prepared as in Example 1, but were in metal working fluid instead of deionized water. MWF concentrate A was a semisynthetic type having about 10 to 15 percent naphthenic/paraffinic oil, about 50 percent water, emulsifying agents, pH adjusting amines, anticorrosive agents, and EP (extreme pressure) agents. MWF concentrate B was a "synthetic" type containing similar types of additives as a semi-synthetic type, but with no oil. ITA solutions were prepared by dilution of a 14.4% aqueous solution of an approximately 75/25 mixture of 5-chloro-2-methyl-3-isothiazolone and 2-methly-3-isothiazolone, the former being considered the active ingredient for these purposes; also present was 9.2 weight percent magnesium chloride and 15.7% magnesium nitrate. Thus the final mixture contained 3-5% of the MWF concentrate, 20-0 ppm active ingredient of the isothiazolone, and the TNB solution.

After mixing the ITA, metal working fluid, and TNB solution, samples were measured by a spectrophotometer after 2 hrs. Results are given Tables 3 and 4.

TABLE 3

| TNB Assay for ITA in MWF Concentration A | |
|---|---|
| ITA Concentration (ppm) | Absorbance at 400 nm |
| 0 | 1.00 |
| 5 | 0.82 |
| 10 | 0.76 |
| 20 | 0.40 |

TABLE 4

| TNB Assay for ITA in MWF Concentration B | |
|---|---|
| ITA Concentration (ppm) | Absorbance at 400 nm |
| 0 | 1.14 |
| 5 | 1.10 |
| 10 | 1.06 |
| 20 | 0.76 |

EXAMPLE 5

Example 5 demonstrates the ability to visually distinguish different concentrations of ITA. Three samples containing 0, 10, and 20 ppm of ITA in deionized water were treated as in Example 1. The color differences were obvious by visual inspection.

While the invention has been described with reference to specific examples and applications, other modifications and uses for the invention will be apparent to those skilled in the art without departing from the spirit and scope of the invention defined in the appended claims.

I claim:

1. A method for determining the concentration of isothiazolones in an aqueous system comprising:
   (a) mixing a known volume of solution to be analyzed for isothiazolone with a volume containing a known quantity of aromatic thiol salt which forms colored solutions for a specified period of time;
   (b) determining color of the resultant solution; and
   (c) comparing the color to a standard of known concentration.

2. Method of claim 1 wherein step (b) is by visual inspection or by use of a spectrophotometer.

3. Method of claim 1 wherein the solution to be analyzed is a sample of fuel.

4. Method of claim 1 wherein said salt is selected from the group consisting of thionitrobenzoates, salts of thiopyridines and salts of thionicotinic acid.

5. Method of claim 4 wherein said salt is a thionitrobenzoate.

6. Method of claim 1 wherein the solution to be analyzed is a sample of cooling tower water.

7. Method of claim 1 wherein the solution to be analyzed is a sample of metal working fluid.

8. Method of claim 1 wherein said salt is selected from the group consisting of 5-thio-2-nitrobenzoate, 2-thiopyridine 4-thiopyridine salt, and 6-thionicotinoate.

* * * * *